(12) United States Patent
Graether

(10) Patent No.: US 9,131,132 B2
(45) Date of Patent: Sep. 8, 2015

(54) PHONE CAMERA MOUNT

(71) Applicant: John M. Graether, Marshalltown, IA (US)

(72) Inventor: John M. Graether, Marshalltown, IA (US)

(73) Assignee: TRANSAMERICAN TECHNOLOGIES INTERNATIONAL, San Ramon, CA (US)

( * ) Notice: Subject to any disclaimer, the term of this patent is extended or adjusted under 35 U.S.C. 154(b) by 0 days.

(21) Appl. No.: 14/478,791

(22) Filed: Sep. 5, 2014

(65) Prior Publication Data

US 2015/0070580 A1    Mar. 12, 2015

Related U.S. Application Data

(60) Provisional application No. 61/874,696, filed on Sep. 6, 2013.

(51) Int. Cl.
*G03B 11/00* (2006.01)
*H04N 5/225* (2006.01)
*B62J 11/00* (2006.01)
*A61B 3/14* (2006.01)

(52) U.S. Cl.
CPC ............... *H04N 5/2251* (2013.01); *A61B 3/14* (2013.01); *B62J 11/00* (2013.01)

(58) Field of Classification Search
USPC .......................................................... 396/544
See application file for complete search history.

(56) References Cited

U.S. PATENT DOCUMENTS

| 4,283,038 | A | * | 8/1981 | Kurtz ............................ 248/478 |
| 4,623,102 | A | * | 11/1986 | Hough, Jr. ................... 248/68.1 |
| 5,407,113 | A | | 4/1995 | Golliher |
| 5,794,906 | A | * | 8/1998 | Harris et al. .................. 248/317 |
| 6,401,943 | B1 | * | 6/2002 | Root ............................... 211/65 |
| 6,572,063 | B1 | * | 6/2003 | Gitelman et al. ............. 248/314 |
| 6,888,940 | B1 | | 5/2005 | Deppen |
| 7,234,673 | B2 | * | 6/2007 | Graneto, III ............... 248/311.2 |
| 7,922,329 | B1 | | 4/2011 | Graether |
| 8,070,026 | B2 | * | 12/2011 | Wadsworth et al. ......... 224/197 |
| 8,294,014 | B2 | | 10/2012 | Voorhees |
| 8,376,292 | B2 | | 2/2013 | Cicco |
| 8,869,977 | B2 | * | 10/2014 | Nlkosey ...................... 206/39.5 |
| 2011/0222842 | A1 | * | 9/2011 | Schippers ................... 396/428 |
| 2012/0252543 | A1 | * | 10/2012 | Cho ........................... 455/575.8 |
| 2012/0264492 | A1 | | 10/2012 | Stewart |
| 2012/0299318 | A1 | | 11/2012 | Murphy et al. |
| 2013/0020363 | A1 | | 1/2013 | Fraser |
| 2013/0056368 | A1 | | 3/2013 | Loredo |
| 2014/0001060 | A1 | * | 1/2014 | Nikosey ......................... 206/37 |
| 2014/0313377 | A1 | * | 10/2014 | Hampton ..................... 348/241 |

FOREIGN PATENT DOCUMENTS

| EP | 1393980 A2 | 3/2004 |
| EP | 2230770 A1 | 9/2010 |
| EP | 2559746 A1 | 2/2013 |
| WO | 2006071829 A1 | 7/2006 |

* cited by examiner

*Primary Examiner* — Rodney Fuller
(74) *Attorney, Agent, or Firm* — Zarley Law Firm, P.L.C.

(57) ABSTRACT

A camera phone mount having an end wall, an outer wall, an inner wall and an open end that form a cavity that receives a vertical support arm. Attached to the outer surface of the inner wall is an elongated mounting plate. A reusable adhesive pad is attached to an inner surface of the elongated mounting plate.

20 Claims, 4 Drawing Sheets

PHONE CAMERA MOUNT

CROSS REFERENCE TO RELATED APPLICATION

This application claims the benefit of U.S. Provisional Application No. 61/874,696 filed Sep. 6, 2013.

BACKGROUND OF THE INVENTION

The present invention is directed to a phone camera mount and more particularly to a phone camera mount having a reusable adhesive pad. The adhesive pad is fashioned from a polyurethane gel or similar plastic that has an adhesive surface that, when it becomes dull or soiled, can be repeatedly restored by washing it with mild hand soap and water.

With the advent of phone cameras a variety of applications for use have arisen. One such example includes use of a phone camera with a slit lamp as an examination tool for eye practitioners. While phone cameras provide greater ease and convenience for use with a slit lamp, the problem of mounting the phone camera to the slit lamp still remains. Rigid mounts must be phone model specific and with the number of smartphone designs in use they are impractical and rapidly become obsolete. Also, conventional camera phones have limited macro capabilities for near objects and require additional optical aids for improved focus and magnification issues. Another deficiency in the prior art is that all other camera mounts for camera phones presented to date have only allowed the phone to be mounted to the slit lamp ocular thus limiting the photos to that limited field of view.

Therefore, a need exists in the art for a device that addresses these deficiencies.

Presented is a reusable adhesive mount for a camera phone that is infinitely flexible and not only accommodates all current phone designs and camera lens positions, but will readily accept the inevitable changes in future phone designs and dimensions. Also presented is a mounting system that allows the camera to be mounted to the ocular but also provides a stable mount using an accessory external arm for direct external photos and videos that can also incorporate the slit beam. This addition greatly enlarges the range of external photos and videos to include the full face, both eyes simultaneously and all ocular tissues. The ocular mount, with its alignment light shield can be employed on any optical device that has a suitable ocular or concentric adjacent surface that will accept the ring clamp for mounting. Such devices would include YAG lasers, surgical assistant scopes attached to surgical microscopes, lensometers, pathology microscopes, binoculars and telescopes.

Also, the external camera mount camera support arm can be modified to allow it to be attached to a bicycle handlebar or stem so that any smartphone can be positioned for viewing while riding. This adaptation permits the use of various bicycle Apps for monitoring the rider's health parameters and for observing maps and trip statistics provided by a variety of available Apps using GPS data. The secure friction mount allows the smartphone and attached adhesive pad to be instantaneously removed from the hardware when leaving the bicycle.

SUMMARY OF THE INVENTION

A camera phone mount having an end wall, an outer wall, an inner wall and an open end that form a cavity that receives a vertical support arm. Attached to the outer surface of the inner wall is an elongated mounting plate. A reusable adhesive pad is attached to an inner surface of the elongated mounting plate.

DETAILED DESCRIPTION FO THE PREFERRED EMBODIMENTS

Figure 1:
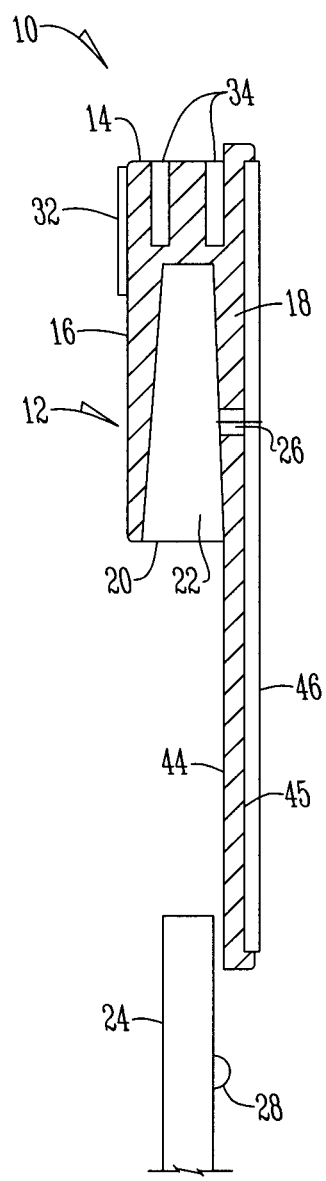
FIG. 1 is a side sectional view of a phone camera mount
Figure 2:
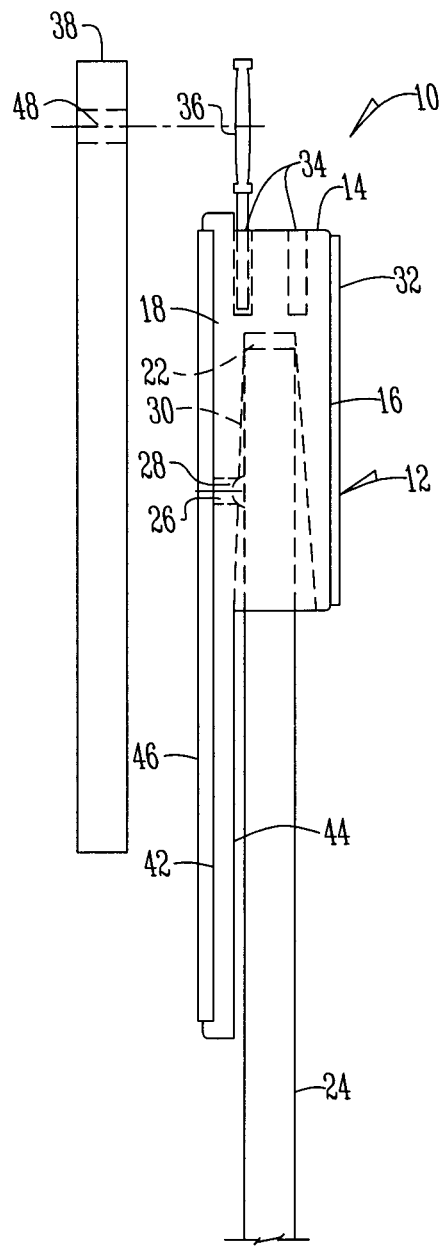
FIG. 2 is a side sectional view of a phone camera mount
Figure 3:
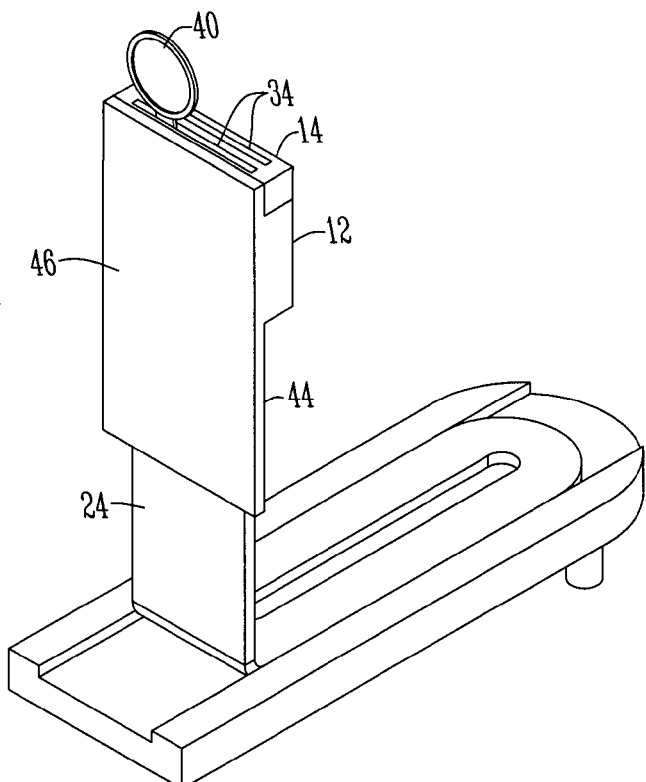
FIG. 3 is a perspective view of a phone camera mount
Figure 4:
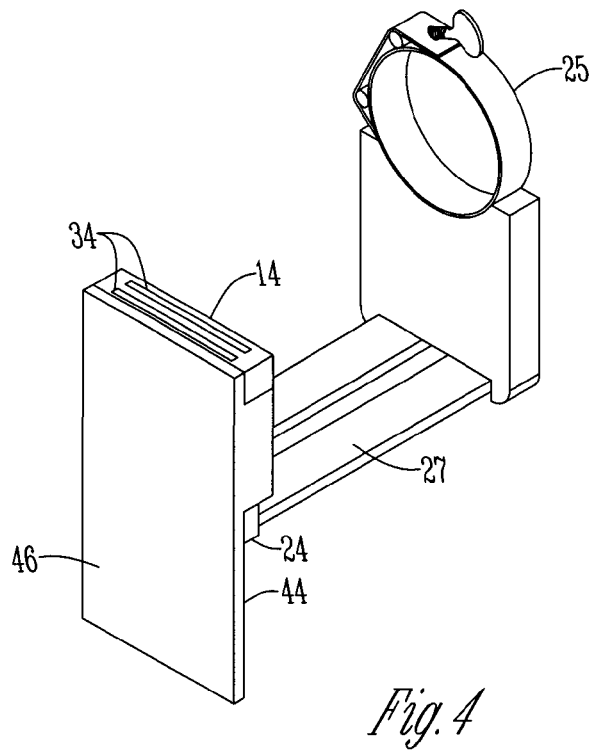
FIG. 4 is a perspective view of a phone camera mount
Figure 5:
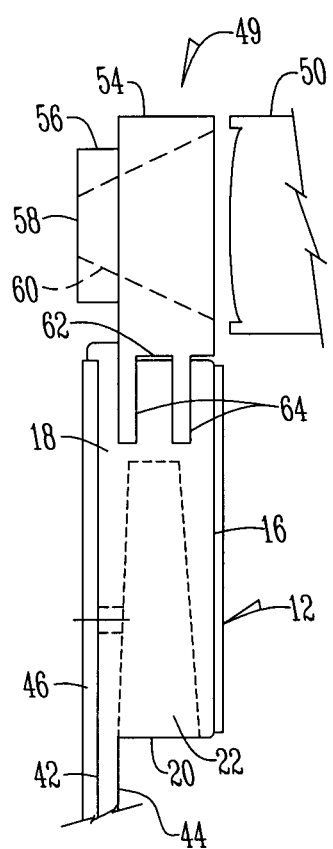
FIG. 5 is a side sectional view of a phone camera mount
Figure 6:
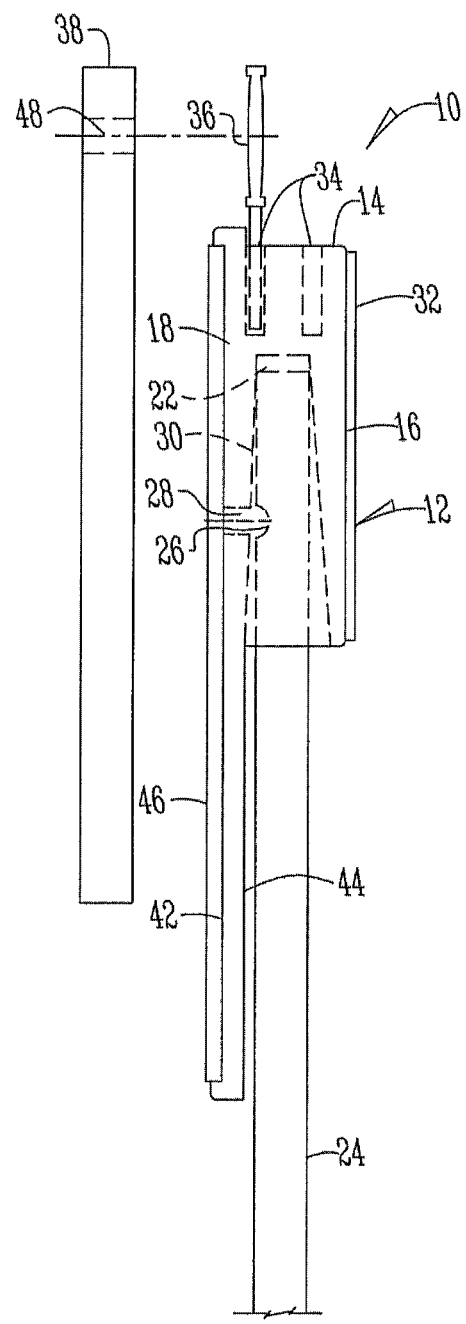
FIG. 6 is side sectional view of a phone camera mount

Referring to the Figures, a camera phone mount 10 has a housing 12 that includes an end wall 14, an outer wall 16, an inner wall 18 and an open end 20 that forms a cavity 22. The cavity 22 is used to receive a vertical support arm 24 from a stand or other device. In one example, the arm 24 is attached to a plate spindle assembly for external photos of an eye. In another example, the arm 24 is part of an ocular clamp fixture for through-the-ocular photos. In still another embodiment the arm is incorporated in a clamp that fits around and is secured to a bicycle handle bar. (Not illustrated)

The inner wall 18 has a detent 26 positioned to receive a protrusion 28 on arm 24 to create a friction or snap fit when the arm 24 is slid within the cavity 22. In an alternative embodiments, the inner wall 18 has the protrusion 28 positioned to receive the detent 26 on the arm 24 to create a friction or snap fit when the arm 24 is slid within the cavity 22. Within the end wall 14 are slots 34. The slots 34 are used to mount lenses 36 to provide focus and magnification of an image and provides multiple locations to accommodate various phone 38 designs. The additional lenses 36 are typically part of the standard refracting lens inventory of an eye practitioner. In addition, the slots 34 are used for filters 40.

Extending from adjacent the end wall 14, along an outer surface 42 of the inner wall 18 and beyond the open end 20 of the housing 12 is an elongated mounting plate 44. Attached to an outer surface 45 of the mounting plate 44 is a reusable adhesive pad 46. The phone 38 is releasably and adhesively mounted to the pad 46.

In operation, the housing 12 is placed over arm 24 such that protuberance 28 is received in detent 26. Next, phone 38 is releasably attached to the reusable adhesive pad 46. When desired, lenses 36 are placed in slots 34 and the phone 38 adjusted so that the camera lens 48 aligns with lens 36. The lenses are easily exchanged to accommodate varying distances between the camera and the subject. By using lenses 36 the quality of the image is enhanced in comparison to the camera phone 38 because the optical enlargement from the lens 36 allows use of a larger portion of the camera's sensor. Also, the focus of the near image induced by the plus power lens, reduces the focus requirements of the phone camera's focusing system further enhancing image quality. As an alternative to individual, fixed-focused plus lenses, a zoom lens system could be added in this location to allow instant changes in magnification and focus of the image without the need to change lenses or reposition the phone camera.

When used with an ocular mount and adjustable clamp 25, the camera phone 38 can be fitted to a variety of ocular designs. A sliding fixture 27 provides adjustment of the camera distance to the ocular. Also, an alignment device 49 is used to align an ocular lens 50 with a lens 48 of the phone 38. The alignment device 49 is of any size and shape and preferably has a main body 54 having an extended section 56 that is generally cylindrical. The extended section 56 has aperture 58 that is generally centrally located. A bore 60 extends from the aperture through the extended section 56 and the main body 54. Preferably the bore 60 tapers outwardly from the aperture 58 forming a conical shape. The conical shape assists in reducing reflection without restricting view. On the bottom 62 of the main body 54 is at least one and preferably two spaced apart mounting tabs 64. The mounting tabs 64 are positioned to be received within slots 34.

To align the ocular lens SO with the camera lens 48 of the phone, the alignment device 49 is attached to the camera phone mount 10 by fitting the mounting tabs 64 into slots 34. The alignment device 49 is then slid within slots 34 such that the ocular lens 50 aligns with and is received within the bore 60. Next, the phone 38 is attached to the adhesive pad 46 of the mounting plate 44 such that the camera phone lens 48 aligns with the aperture 58 of the alignment device 48. Thus, the optical axis of the phone camera lens is made coincident with the optical axis of the ocular 50 to which it is aligned. Once these initial adjustments are made for any specific slit lamp model, mounting any phone camera for subsequent photo sessions will automatically result in accurate alignment of the camera lens with that slit lamp's ocular.

What is claimed is:

1. A camera phone mount; comprising:
    a housing having an end wall, an outer wall, an inner wall, and an open end that forms a cavity that receives a vertical support arm, wherein the end wall has at least one slot;
    an elongated mounting plate attached to an outer surface of the inner wall; and
    a reusable adhesive pad attached to an outer surface of the elongated mounting plate.

2. The mount of claim 1 wherein the at least one slot receives lenses and filters.

3. The mount of claim 2 wherein when a lens is mounted in the at least one slot it aligns with a camera lens.

4. The mount of claim 2 wherein the lens is a zoom lens system.

5. The mount of claim 1 wherein the inner wall has a protrusion positioned to receive a detent on the vertical support arm.

6. The mount of claim 1 wherein an alignment device is received in the at least one slot.

7. The mount of claim 6 wherein the alignment device has a main body having an extended section, a bore extending from an aperture in the extended section through the extended section and the main body, and at least one mounting tab on a bottom of the main body.

8. The mount of claim 7 wherein the bore tapers outwardly from the aperture forming a conical shape.

9. The mount of claim 7 wherein the at least one tab is received by the at least one slot.

10. The mount of claim 6 wherein the alignment device has a main body having an extended section, a bore extending from an aperture in the extended section through the extended section and the main body, and at least two spaced apart mounting tabs on a bottom of the main body.

11. The mount of claim 1 wherein the vertical support arm is attached to a plate spindle assembly.

12. The mount of claim 1 wherein the vertical support arm is incorporated in an ocular clamp fixture.

13. The mount of claim 1 wherein the vertical support arm is incorporated in a clamp removably fitted on a bicycle handle bar.

14. The mount of claim 1 wherein the at least one slot receives lenses.

15. The mount of claim 1 wherein the at least one slot receives filters.

16. The mount of claim 1 further comprising a phone having a camera releasably attached to the reusable adhesive pad.

17. The mount of claim 1 further comprising a sliding fixture attached to the housing and an ocular mount.

18. The mount of claim 1 wherein the vertical support arm has a protrusion positioned to receive a detent on the inner wall.

19. A camera phone mount; comprising:
    a housing having an end wall, an outer wall, an inner wall, and an open end that forms a cavity that receives a vertical support arm, wherein the vertical support arm has a protrusion positioned to receive a detent on the inner wall;
    an elongated mounting plate attached to an outer surface of the inner wall; and
    a reusable adhesive pad attached to an outer surface of the elongated mounting plate.

20. A camera phone mount; comprising:
    a housing having an end wall, an outer wall, an inner wall, and an open end that forms a cavity that receives a vertical support arm, wherein the inner wall has a protrusion positioned to receive a detent on the vertical support arm;
    an elongated mounting plate attached to an outer surface of the inner wall; and
    a reusable adhesive pad attached to an outer surface of the elongated mounting plate.

* * * * *